US007175998B2

(12) United States Patent
Bateman

(10) Patent No.: US 7,175,998 B2
(45) Date of Patent: Feb. 13, 2007

(54) **STABLE *ACANTHAMOEBA* PROTEIN EXPRESSION SYSTEMS**

(75) Inventor: Erik Bateman, Williston, VT (US)

(73) Assignee: The University of Vermont and State Agriculture College, Burlington, VT (US)

( * ) Notice: Subject to any disclaimer, the term of this patent is extended or adjusted under 35 U.S.C. 154(b) by 0 days.

(21) Appl. No.: 11/155,446

(22) Filed: Jun. 17, 2005

(65) Prior Publication Data

US 2006/0003415 A1 Jan. 5, 2006

Related U.S. Application Data

(60) Provisional application No. 60/582,581, filed on Jun. 23, 2004.

(51) Int. Cl.

| | |
|---|---|
| ***C12N 15/85*** | (2006.01) |
| ***C12N 15/87*** | (2006.01) |
| ***C12N 15/63*** | (2006.01) |
| ***C12N 15/64*** | (2006.01) |
| *C12N 5/10* | (2006.01) |
| *C12N 1/04* | (2006.01) |

(52) U.S. Cl. ................... 435/69.1; 435/320.1; 435/455

(58) Field of Classification Search ..................... None
See application file for complete search history.

(56) References Cited

OTHER PUBLICATIONS

Kong, et al., "Intracellular Localization and Dynamics of Myosin-II and Myosin-IC in Live *Acanthamoeba* by Transient Transfection of EGFP Fusion Proteins", Journal of Cell Science 115(24):4993-5002 (2002).

Lefebre, et al., "Construction and Evaluation of Plasmid Vectors Optimized for Constitutive and Regulated Gene Expression in Burkholderia Cepacia Complex Isolates", Applied and Environmental Microbiology 68(12):5956-5964 (2002).

Yin, et al., "Stable Transfection of *Acanthamoeba*", Candian Journal of Microbiology, 43:239-244 (1997).

Hu et al., "An *Acanthamoeba polyubiquitin* Gene and Application of its Promoter to the Establishment of a Transient Transfection System" 1351:126-136 (1997).

*Primary Examiner*—David Guzo
(74) *Attorney, Agent, or Firm*—Gregory B. Butler, Esq.

(57) ABSTRACT

The disclosure concerns stable expression systems for production of a protein comprising: a) a species of *Acanthamoeba* as a host organism; b) a DNA vector which comprises a selection marker gene which codes for a protein which, after transformation of the host organism, allows selection of positive transformants, where expression of the selection marker gene is controlled by at least one genetic regulatory element which is homologous in the host organism; and c) a DNA vector which comprises a heterologous gene for the expression of a heterologous protein, where the expression of the protein is controlled by at least one genetic regulatory element which is homologous to the host organism.

18 Claims, 9 Drawing Sheets

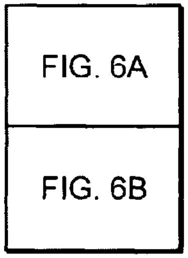

FIG. 6

(SEQ ID NO: 1)

Acanthamoeba TBP Gene Promoter Region

Accession Number: M93340. Acanthamoeba cast...[gi:16876482]

```
CTGCAGCACT GCCCGGCAGC CAAGGCCGAA AGCGAACAGC AGATGGTCGC CGCCTACTCT 61
CACCTTCTCG AGAAGATTGC CGAGCAGCAG CACACCACCT CTACTCACAG CTCCCTCGTC 121
GAAGAGTAAG CAGGTACCGT TCAGTGTGAC AGTGTACGCG GATGAGACAG AATGTAAGTT 181
TTAGGTGCCC GCAGAGGAGA CAGATGACAG AAGAGATGGT GGTGAAGATG ATGGTGATGA 241
TGGTGGTGGA GGAGGTGGCT GTCCATCAGC AGTCAGCGAG CTCGGCCGAG TAGAGAGCGG 301
GCTCCAGCGT TGGGTTGTCG TCCATGAAGA AGAGCTTCCA CTTCTGTCCG GGCGAGATAG 361
CGCCCTGGTT GAAGAAGATC CACCGCGAGG GCTGGTCGTG GGGGCCGTTC GCCGGGTTAT 421
TGATGTTGAA CTTTGTATCC ACGTCGCACG CGCAGCAGTT CTGCATATAC CACTTCTGCG 481
CAGGAGCGGA ATATACGGGA GACCCGGGTG ATGGTGAAAA CATGATGGTG AGATTACATA 541
ACAACTTCAA ATCTTGAAGA TGGAGTTGAA AGAGATTGAA CAAAGGTTAC CTGGTCGTCA 601
TCTTTGAAGT AGGTGAAGCA GGTGTTGACT TCGTGCTGTT CGATTCCGGG GCAGTGAACC 661
```

FIG. 6A

GAGGCGGGGG GAGCGTAGGC GAAGCGCTTG TTGGGGTTGA GGCGCTTGAG CTTGCCCACT 721
CCGCCCTCGG GGAGGATCCC ATCTTCGACC AGCTCGCGCG TAGCGATCAG GCCTTCCATG 781
ACGAAGTCTT CCTCGAACCA CATCGGCTCT TCATCGACGT TGCCCTTCAC CGTGCCCACC 841
GCGAATAACG CAAGGCCGCA CAGGACCAGC GCCAGGCAAA GGGCGAGCCT CATCTTCGTG 901
AAGCTGAAGC TGGGTTGTTG CGGGAAACGA *CGCCTTGCAA CAAGCTGAGA AAAAACCAGG 961*
*ATCGGCAAGG AAGGATTTTC AACGGAAACG TTGGCATCAC CGGGTATAAA AAGGGGCCAA 1021*
*TTTTTTTGTT GATTTGTTGC GCGAATTCTT GCTTTCGGCA TCGAATTCAA GGGAGAAGGA 1081*
*GTCGATTCAC ACATACAACA AGATG*

Note, only the sequence upstream from the ATG translation initiation codon is shown. The transcription start site is shown in green. The fragment used in the expression constructs (-110 to the ATG codon) is in bold.

The TBP promoter is regulated by three distinct sequences. 1. An upstream sequence between -97 and
-77 relative to the transcription start site positively regulates transcription by binding an activator protein called TPBF. 2. The TATAAA box at -30 is absolutely required for transcription and interacts with the protein TBP. 3. The sequence between the TATA box and the transcription start site negatively regulates transcription when the levels of TPBF are high.

FIG. 6B (SEQ ID NO: 2)

Acanthamoeba CSP21 Promoter Sequence

Accession Number: AB023410. Acanthamoeba cast...[gi:6682866]

CTCGAGGGCG GCAGCGTAGC GGGCAAGACC ACCCCGTTGT CCGCCAGCAG CTCATCATCT 61
TCGACCTCCA CCTCCTCTAC CTCCAGCAGC TCGTTGACCA CAGTCAAGAA GTTCGACTTC 121
ACCTCCATCG CCATCAACAC CACCGAGGAC CTCAAGCTCT CGTGGAAGGA CTCGCTGCTC 181
GACTCGATGA CCTTTGCCCA CACCGACGAC GCCGAGGCCA AGGAGTCCGC CGCAGGCGAC 241
AAGGAAGAAG AGGCCGACTT CTGCTTCGAC CTGGGCAAGT CGAGCGACGA CGAGCGGTGC 301
CTCGAGGAGA TACCACAGGA GATGGTCAGA GAACTGACCG AGCTGCGCTC CTACAACTCT 361
ACGCTCCAGG ACATGATCAA GGACGTCCAG CAGTTCAACT CCTACCAGAG GAAGAAGCGT 421
CGCCAGTGGG AGCTCAGCAA GATCAACAAC GGCACCAGCG CCTCCACCAC CCCCGGTTCG 481
GGTGCGCTCG CCGCCACCGC CGCCCCCAGC GACGCCCTGC CCCAGTGGCT CGTGAGCGAC 541
TTCTCCAGCC TCTCCAACAA GCTCGTCGAC CTTTCGTCCG ACCCGACTCA CGCCTCTTCC 601
ACTTCATCAT CGTCGTCGAT CTCCTCCTCG GCCGGCTCGG CCGGTGGCGC CGCTCACCAC 661
GGCCACGGCG GCCGCTCTGC CGGCGAGGAG GGCGAGATGG ACTACCTCGG CGCCTGGCAG 721
CAGTCGATGG CCAACCACGG CGCCCCGCTC CAGCTGCCGA CGCAGCTCGC GCTCCTCGCG 781
GGCCACCACT CGATGCTGCA GCTCCCGGGT CAGCTGACGA CCCAGCAGCA GGCCCAGCCT 841
CAGCAGCAGG TCCAGCAGCC CCTCGCGGCC AACAACGCGG CGGCCAACGC GCCCCAGAGC 901
GGGCCTGCTC CCTTCACCAC GTCGCTGCCC TTCACCGAAG TCTGAACGAC GTTGATGGAG 961
GAGACATAGG CACTACAACT CTACAAGACC ACTTTCGACG ACTGCTGCGA ATCCAGCGAA 1021
CAGGGCGCAC ACAACGTAGG GGGGGACGTG GGGAGACGGA GCACGCAAAC ATACGACCAG 1081
TACCAAGGCA CATGACCAGT ACTTTATGTA AACGTTTGAA GAGAGCAAGT ACAACCCTGT 1141
ACGCCCCAAA AAGTACACAC CTTGGCACTT TCGTCCGCGT CTCTTCTTCG TGGCCACAAT 1201
TCATGGAGAA GAAGGTGGCG CCCGGCCCTC GAAATTCTGG AGATTGGGTG AGAGCTGTAC 1261
CATGTCAACC AATGCCTGGA GGGTGTTGTA GGGCCTCCAG TTCCACTTGT GGGCCGACCA 1321
**ATGGCCTGTG TTCTTGGCAA CTATAAGAAG GTCACCCACA *CCCACCCCAT CCTCCACCAC 1381***
***CGCACCCAAC CAACAACCAA CCTACTACCA ACTATCTGAA* GATG**

Note: Only the promoter sequence as far as the ATG translation initiation signal is shown. The transcription start site is shown in bold and underlined. The fragment used for the cyst-specific expression construct is shown in bold.

FIG. 7

SEQUENCE LISTING

<160> NUMBER OF SEQ ID NOS: 13

<210> SEQ ID NO 1
<211> LENGTH: 1105
<212> TYPE: DNA
<213> ORGANISM: Acanthamoeba castellanii

<400> SEQUENCE: 1

```
ctgcagcact gcccggcagc caaggccgaa agcgaacagc agatggtcgc cgcctactct     60
caccttctcg agaagattgc cgagcagcag cacaccacct ctactcacag ctccctcgtc    120
gaagagtaag caggtaccgt tcagtgtgac agtgtacgcg gatgagacag aatgtaagtt    180
ttaggtgccc gcagaggaga cagatgacag aagagatggt ggtgaagatg atggtgatga    240
tggtggtgga ggaggtggct gtccatcagc agtcagcgag ctcggccgag tagagagcgg    300
gctccagcgt tgggttgtcg tccatgaaga agagcttcca cttctgtccg ggcgagatag    360
cgccctggtt gaagaagatc caccgcgagg gctggtcgtg ggggccgttc gccgggttat    420
tgatgttgaa ctttgtatcc acgtcgcacg cgcagcagtt ctgcatatac cacttctgcg    480
caggagcgga atatacggga gacccgggtg atggtgaaaa catgatggtg agattacata    540
acaacttcaa atcttgaaga tggagttgaa agagattgaa caaaggttac ctggtcgtca    600
tctttgaagt aggtgaagca ggtgttgact tcgtgctgtt cgattccggg gcagtgaacc    660
gaggcggggg gagcgtaggc gaagcgcttg ttggggttga ggcgcttgag cttgcccact    720
ccgccctcgg ggaggatccc atcttcgacc agctcgcgcg tagcgatcag gccttccatg    780
acgaagtctt cctcgaacca catcggctct tcatcgacgt tgcccttcac cgtgcccacc    840
gcgaataacg caaggccgca caggaccagc gccaggcaaa gggcgagcct catcttcgtg    900
aagctgaagc tgggttgttg cgggaaacga cgccttgcaa caagctgaga aaaaaccagg    960
atcggcaagg aaggattttc aacggaaacg ttggcatcac cgggtataaa aaggggccaa   1020
tttttttgtt gatttgttgc gcgaattctt gctttcggca tcgaattcaa gggagaagga   1080
gtcgattcac acatacaaca agatg                                          1105
```

<210> SEQ ID NO 2
<211> LENGTH: 1424
<212> TYPE: DNA
<213> ORGANISM: Acanthamoeba castellanii

<400> SEQUENCE: 2

```
ctcgagggcg gcagcgtagc gggcaagacc accccgttgt ccgccagcag ctcatcatct     60
tcgacctcca cctcctctac ctccagcagc tcgttgacca cagtcaagaa gttcgacttc    120
acctccatcg ccatcaacac caccgaggac ctcaagctct cgtggaagga ctcgctgctc    180
gactcgatga cctttgccca caccgacgac gccgaggcca aggagtccgc cgcaggcgac    240
aaggaagaag aggccgactt ctgcttcgac ctgggcaagt cgagcgacga cgagcggtgc    300
ctcgaggaga taccacagga gatggtcaga gaactgaccg agctgcgctc ctacaactct    360
acgctccagg acatgatcaa ggacgtccag cagttcaact cctaccagag gaagaagcgt    420
cgccagtggg agctcagcaa gatcaacaac ggcaccagcg cctccaccac ccccggttcg    480
ggtgcgctcg ccgccaccgc cgcccccagc gacgccctgc cccagtggct cgtgagcgac    540
ttctccagcc tctccaacaa gctcgtcgac ctttcgtccg acccgactca cgcctcttcc    600
acttcatcat cgtcgtcgat ctcctcctcg gccggctcgg ccggtggcgc cgctcaccac    660
```

-continued

```
ggccacggcg gccgctctgc cggcgaggag ggcgagatgg actacctcgg cgcctggcag    720

cagtcgatgg ccaaccacgg cgccccgctc cagctgccga cgcagctcgc gctcctcgcg    780

ggccaccact cgatgctgca gctcccgggt cagctgacga cccagcagca ggcccagcct    840

cagcagcagg tccagcagcc cctcgcggcc aacaacgcgg cggccaacgc gccccagagc    900

gggcctgctc ccttcaccac gtcgctgccc ttcaccgaag tctgaacgac gttgatggag    960

gagacatagg cactacaact ctacaagacc actttcgacg actgctgcga atccagcgaa   1020

cagggcgcac acaacgtagg gggggacgtg gggagacgga gcacgcaaac atacgaccag   1080

taccaaggca catgaccagt actttatgta aacgtttgaa gagagcaagt acaaccctgt   1140

acgccccaaa aagtacacac cttggcactt tcgtccgcgt ctcttcttcg tggccacaat   1200

tcatggagaa gaaggtggcg cccggccctc gaaattctgg agattgggtg agagctgtac   1260

catgtcaacc aatgcctgga gggtgttgta gggcctccag ttccacttgt gggccgacca   1320

atggcctgtg ttcttggcaa ctataagaag gtcacccaca cccaccccat cctccaccac   1380

cgcacccaac caacaaccaa cctactacca actatctgaa gatg                    1424


<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6x His tag

<400> SEQUENCE: 3

His His His His His His
  1               5


<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Met Gly Tyr Pro Tyr Asp Val Pro Asp Tyr Ala Val His His His His
  1               5                  10                  15

His His


<210> SEQ ID NO 5
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5

cagatatcaa acgacgcctt gcaacaag                                        28


<210> SEQ ID NO 6
<211> LENGTH: 29
<212> TYPE: DNA
<213> ORGANISM: Artificial Sequence
<220> FEATURE:
<223> OTHER INFORMATION: Description of Artificial Sequence: Synthetic
      primer
```

-continued

```
<400> SEQUENCE: 6

cagatatctt gttgtatgtg tgaatcgac                                            29

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7

gaggtaccaa acgacgcctt gcaacaag                                             28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8

gaggtaccga aacgttggca tcaccggg                                             28

<210> SEQ ID NO 9
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9

cgaccatggc ttgttgtatg tgtgaatcga c                                         31

<210> SEQ ID NO 10
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10

gctgtacaag tacccctacg acgtgcccga ctac                                      34

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11

gctctagagt cgcggccgct ttaggtcttc ttgtactc                                  38

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
```

-continued

```
gatccggtac ccaactctac aagaccactt tcg                             33


<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

ggatcccatg gcttcagata gttggtagta gg                              32
```

STABLE *ACANTHAMOEBA* PROTEIN EXPRESSION SYSTEMS

This application claims the benefit of U.S. Provisional Application Ser. No. 60/582,581, filed Jun. 23, 2004, which is herein incorporated by reference.

STATEMENT OF RIGHTS TO INVENTIONS MADE UNDER FEDERALLY SPONSORED RESEARCH

This work was supported by the following grant from the National Institutes of Health, National Eye Institute Grant No: EY08706. The government may have certain rights in the invention.

FIELD OF INVENTION

The present invention generally relates to the area of protein expression. More particularly, the invention relates to systems for expressing proteins of human or veterinary therapeutic value.

BACKGROUND OF THE INVENTION

Several publications and patent documents are cited throughout the specification in order to describe the state of the art to which this invention pertains. Full citations for those references that are numbered can be found at the end of the specification. Each citation is incorporated herein as though set forth in full.

The rapid developments in recombinant DNA techniques have resulted in the identification and isolation of many novel genes, some of known function and some of unknown function. Invariably there is a need to express the gene in a heterologous cell system in order to produce material for structure-function studies, diagnostic reagents such as monoclonal or polyclonal antibodies and material for in vivo activity testing and therapy.

Several alternative systems for the expression of foreign genes have been developed including systems based upon mammalian cells, insect cells, fungal cells, bacterial cells and transgenic animals or plants. The choice of expression system for a given gene depends upon the likely features of the encoded protein, for example any post-translational protein modifications needed for biological activity, as well as the objective of the study. Other important considerations for the investigator are the facilities available, time and cost involved in generating the amounts of recombinant protein required.

The most widely used and convenient system for the production of foreign proteins remains that based on the prokaryote *Escherichia coli*. The advantages of this system comprise the ease of gene manipulation, the availability of reagents including gene expression vectors, the ease of producing quantities of protein (up to a gram in simple shake-flask culture), speed and the high adaptability of the system to express a wide variety of proteins.

Unfortunately, however, a problem encountered with *E. coli* based expression systems is the difficulty of producing material which is acceptable for therapeutic use. Some heterologous gene products fail to attain their correct three-dimensional conformation in *E. coli* while others become sequestered in large insoluble aggregates or “inclusion bodies” when overproduced. Major denaturant-induced solubilization methods followed by removal of the denaturant under conditions that favor refolding are often required to produce a reasonable yield of the recombinant protein. Selection of ORFs from structural genomics projects have also shown that only about 20% of the genes expressed in *E. coli* render proteins that were soluble or correctly folded. These numbers are startlingly disappointing especially given that most scientists rely on *E. coli* for initial attempts to express gene products. Furthermore, the use of complex media, antibiotic selection and potentially hazardous inducers may potentially render products such as recombinant antibody fragments produced by *E. coli* fermentation technology unacceptable to the regulatory authorities for clinical applications. Evidence demonstrating clearance of these agents from the final product must be provided in order to secure regulatory clearance. Clearance of these agents, and especially demonstrating such clearance, is expensive. It is therefore desirable that an expression system should avoid the three above-mentioned problems.

Expression in mammalian cells is often preferred for manufacturing of therapeutic proteins, since post-translational modifications in such expression systems are more likely to resemble those occurring on endogenous proteins in a mammal, than the type of post-translational modifications that occur in microbial expression systems Several vectors are available for expression in mammalian hosts, each containing various combinations of cis- and in some cases trans-regulatory elements to achieve high levels of recombinant protein in a minimal time frame. However, despite the availability of numerous such vectors, the level of expression of a recombinant protein achieved in mammalian systems is often lower than that obtained with a microbial expression system. Additionally, because only a small percentage of cloned, transfected mammalian cells express high levels of the protein of interest, it can often take a considerably longer time to develop useful stably transfected mammalian cell lines than it takes for microbial systems.

There are a number of reasons for the lack of efficient recombinant protein expression in a host, including, for example, short half life, improper folding or compartmentalization and codon bias. While the Human Genome project has successfully created a DNA “map” of the human genome, the development of protein expression technologies that function uniformly in different expression platforms and for all the protein motifs has not yet been achieved. It would be desirable and advantageous to have alternative stable expression systems available when other systems for protein expression are unsuitable for one reason or another.

SUMMARY OF THE INVENTION

The present invention relates to stable transfection systems of *Acanthamoeba castellanii* using plasmids which confer resistance to neomycin G418. Expression of neomycin phosphotransferase is driven by the *Acanthaomeba* TBP gene promoter, and can be monitored by cell growth in the presence of neomycin G418 or by Western analysis. Transfected cells can be passaged in the same manner as control cells and can be induced to differentiate into cysts, in which form they maintain resistance to neomycin G418. Expression of GFP or an HA-tagged GFP-TBP fusion can be driven from the same plasmid, using an additional copy of the *Acanthamoeba* TBP gene promoter or a deletion mutant. GFP expression can also be driven by the cyst-specific CSP21 gene promoter, which is completely repressed in growing cells but strongly induced in differentiating cells. The present invention demonstrates the utility of the neomycin resistance based plasmids for stable transfection of *Acanthamoeba* and the production of therapeutic polypeptides.

As such, the present invention relates to stable expression systems for production of a protein comprising: a) a host organism selected from the group consisting of the species of *Acanthamoeba*; b) a DNA vector which comprises a selection marker gene which codes for a protein which, after transformation of the host organism, allows selection of positive transformants and is selected from the group consisting of antibiotic resistance genes or of genes which encode proteins which are capable of a color-forming reaction, where expression of the selection marker gene is controlled by at least one genetic regulatory element which is homologous in the host organism; and c) a DNA vector which comprises a heterologous gene for the expression of a heterologous protein, where the expression of the protein is controlled by at least one genetic regulatory element which is homologous to the host organism.

Other embodiments of the present invention include DNA vectors which can be used to develop stable protein expression systems in species of *Acanthamoeba* and kits containing such stable expression systems and DNA vectors.

BRIEF DESCRIPTION OF THE FIGURES

FIG. 6 represents the *Acanthamoeba* TBP Gene Promoter Region DNA sequence (SEQ ID No. 1).

FIG. 7 represents the *Acanthamoeba* CSP21 Promoter DNA Sequence (SEQ ID No. 2).

DETAILED DESCRIPTION OF THE INVENTION

Figure 1A:
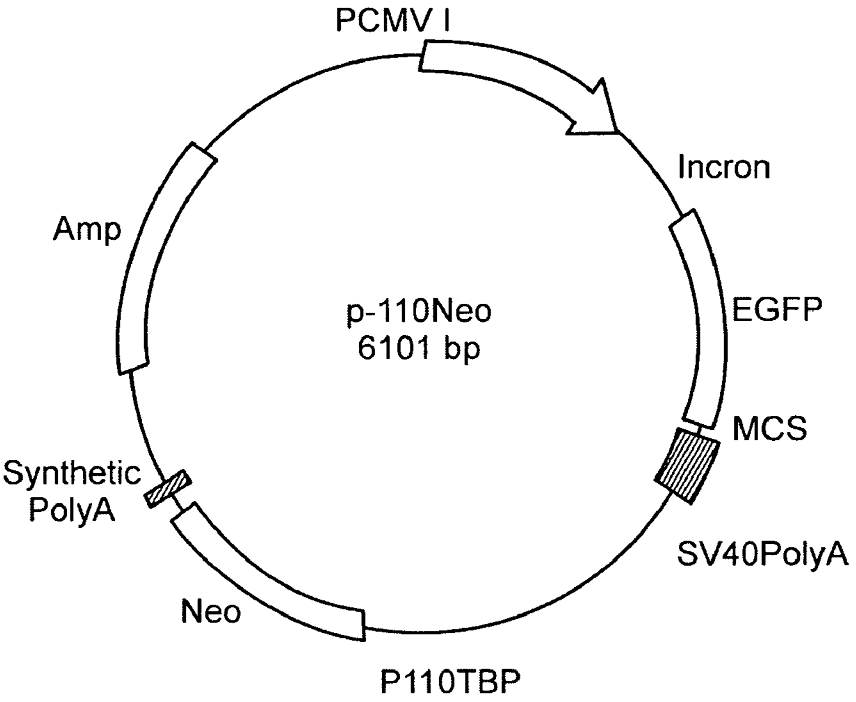
FIG. 1 represents a) diagram of plasmid p-110Neo showing the positions of the TBP gene promoter and the neomycin phosphotransferase gene; b) Photomicrograph of control, untransfected cells; c) Photomicrograph of transfected cells grown in the presence of neomycin G418; d) Western analysis of cell lysates from: Lane 1), control cells; lane 2), cells transfected with p-110Neo.

It is understood that this invention is not limited to the particular materials and methods described herein. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

*Acanthamoeba* Host Cells

*Acanthamoeba castellanii* is a small free-living amoeba associated with the disease *Acanthamoeba* keratitis (1, 2), and with several bacterial diseases by virtue of a symbiotic or parasitic relationship between *Acanthamoeba* and various pathogenic bacteria (3). *Acanthamoeba* has been a useful organism for studies on gene expression (4–13) and on numerous components of the cytoskeleton involved in motility and other processes (14–24) as well as mechanisms and phylogeny of pathogenicity (25–34). However, several avenues of analysis have been precluded by the lack of transient or stable transfection systems, even though procedures for introducing proteins into living *Acanthamoeba* were described several years ago (35). Methods for transfection of the related species *Acanthamoeba polyphaga* have been reported, but these have not been generally useful for transfection of *Acanthamoeba castellanii* for reasons that are unclear (36, 37). Kong and Pollard recently described a method for transient transfection of *Acanthamoeba* (38), and we have obtained similar results using their plasmid pUbGMIIt as well as several derivatives in which GFP expression is driven by the TBP, TPBF or CSP21 gene promoters (unpublished results). However, the efficiency of transfection is low (~5% or less), which complicates quantification of results when it is desirable to compare the efficiency, for example, of promoter mutants.

The present invention relates to stable expression systems for production of a protein comprising: a) a host organism selected from the group consisting of the species of *Acanthamoeba*; b) a DNA vector which comprises a selection marker gene which codes for a protein which, after transformation of the host organism, allows selection of positive transformants and is selected from the group consisting of antibiotic resistance genes or of genes which encode proteins which are capable of a color-forming reaction, where expression of the selection marker gene is controlled by at least one genetic regulatory element which is homologous in the host organism; and c) a DNA vector which comprises a heterologous gene for the expression of a heterologous protein, where the expression of the protein is controlled by at least one genetic regulatory element which is homologous to the host organism.

Other embodiments of the present invention include DNA vectors which can be used to develop stable protein expression systems in species of *Acanthamoeba* and kits containing such stable expression systems and DNA vectors.

Expression of Recombinant Proteins

As used herein, the term 'expression vector' is understood to describe a vector that comprises various regulatory elements, described in detail below, that are necessary for the expression of recombinant, heterologous proteins in *Acanthamoeba* cells. The expression vector can include signals appropriate for maintenance in *Acanthamoeba* cells, and/or the expression vector can be integrated into a chromosome.

Recombinant expression vectors may include a coding sequence encoding a protein of interest (or fragment thereof), human polypeptides, ribozymes, antisense RNAs and the like. Preferably, the coding sequence encodes a therapeutic protein or peptide. The coding sequence may be synthetic, a cDNA-derived nucleic acid fragment or a nucleic acid fragment isolated by polymerase chain reaction (PCR). The coding sequence is operably linked to suitable transcriptional or translational regulatory elements derived from mammalian, viral or insect genes. Such regulatory elements include a transcriptional promoter, a sequence encoding suitable mRNA ribosomal binding sites, and sequences which control the termination of transcription and translation (i.e., a polyadenylation signal).

Expression vectors may also comprise non-transcribed elements such as a suitable promoter and/or enhancer linked to the gene to be expressed, other 5' or 3' flanking non-transcribed sequences, 5' or 3' non-translated sequences such as ribosome binding sites, a polyadenylation site, splice donor and acceptor sites, and transcriptional termination sequences. An origin of replication that confers the ability to replicate in a host, and a selectable gene to facilitate recognition of transfectants, may also be incorporated.

DNA regions are operably linked when they are functionally related to each other. Operably linked means contiguous and in reading frame. A promoter is operably linked to a coding sequence if it controls the transcription of the sequence; and a ribosome binding site is operably linked to a coding sequence if it is positioned so as to permit translation.

The term "promoter" as used herein refers to a DNA sequence that precedes a gene in a DNA polymer and provides a site for initiation of the transcription into mRNA. Preferred promoters of the present invention include the homologous TBP gene promoter (See FIG. 6; SEQ ID No. 1; Accession Number: M93340) as fully described in the following publications: 1) Liu, F. and Bateman, E. (1992) *Acanthamoeba castellanii* RNA polymerase II transcription in vitro. Accurate initiation at the adenovirus major late promoter. Gene 120, 143–149; 2) Wong, J.-M., Liu, F. and Bateman, E. (1992) Isolation of genomic DNA encoding transcription factor TFIID from *Acanthamoeba castellanii*: characterization of the promoter. Nucleic Acids Research 20, 4817–4824; 3) Liu, F. and Bateman, E. (1993) An upstream promoter element of the *Acanthamoeba castellanii* TBP gene binds a DNA sequence specific transcription activating protein, TPBF. Nucleic Acids Research 21, 4231–4329; 4) Liu, F. and Bateman, E. (1994) Purification and characterization of TATA-binding protein promoter binding factor. A regulatory factor of the TBP gene. J. Biol. Chem. 269, 18541–18548; and 5) Huang, W. and Bateman, E. (1995) Cloning, expression and characterization of TPBF, a transcription activator of the *Acanthamoeba* TATA-binding protein gene. J. Biol. Chem. 270,28839–28847.

Another preferred promoter of the present invention includes the CSP21 gene promoter (see FIG. 7; SEQ ID No. 2; Accession Number: AB23410) which can be used to support inducible gene expression the CSP21 gene and promoter is fully described in Hirukawa, Y., H. Nakato, S. Izumi, T. Tsuruhara, and S. Tomino. 1998. Structure and expression of a cyst-specific protein of *Acanthamoeba castellanii*. Biochim. Biophys. Acta. 1398:47–56 and Chen, L., Orfeo, T., Gilmartin, G. and Bateman, E. (2004) Mechanism of cyst specific protein 21 mRNA induction during *Acanthamoeba* differentiation. BBA 1691, 23–31. The CSP21 promoter is tightly repressed during cell growth by a repressor which interacts with DNA sequences between the transcription start site and the ATG initiation codon. It is believed that the repressor is inactivated during encystment, permitting the differentiation-specific expression of CSP21 or in the present case EGFP.

Promoters that are not suitable for the present invention include the SV40 early promoter and enhancer, the Roux Sarcoma virus LTR promoter and a cytomegalovirus promoter. These are all strong promoters in mammalian systems, but failed to express either neomycin phosphotransferase or eGFP in the *Acanthamoeba* system.

Preparation of Transfected *Acanthamoeba* Cells

The term "stable transfection" or "stably transfected" refers to the introduction and integration of foreign DNA into the genome of the transfected *Acanthamoeba* cell. The term "stable transfectant" refers to a cell which has stably integrated foreign DNA into the genomic DNA. Alternatively, "stable transfection" of the foreign DNA can occur by the incorporation of genome independent plasmids.

Several transfection protocols are known in the art, and are reviewed in Kaufman, R. J., Meth. Enzymology 185: 537 (1988). The transfection protocol chosen will depend on the nature of the protein of interest, and can be chosen based upon routine experimentation. The basic requirements of any such protocol are first to introduce DNA encoding the protein of interest into a suitable *Acanthamoeba* host cell, and then to identify and isolate host cells which have incorporated the heterologous DNA in a stable, expressible manner.

One commonly used method of introducing heterologous DNA is calcium phosphate precipitation, for example, as described by Wigler et al. (Proc. Natl. Acad. Sci. USA 77:3567, 1980). DNA introduced into a host cell by this method frequently undergoes rearrangement, making this procedure useful for cotransfection of independent genes.

More recently, several reagents useful for introducing heterologous DNA into a mammalian cell have been described. These include Lipofectin Reagent, Lipofectamine Reagent (Gibco BRL, Gaithersburg, Md.) and Superfect Reagent (Qiagen). All of these reagents are commercially available reagents and are used to form nucleic acid complexes which, when applied to cultured cells, facilitate uptake of the nucleic acid into the cells.

Transfection of cells with heterologous DNA and selection for cells that have taken up the heterologous DNA and express the selectable marker results in a pool of transfected cells. Individual cells in these pools will vary in the amount of DNA incorporated and in the chromosomal location of the transfected DNA. After repeated passage, pools frequently lose the ability to express the heterologous protein. To generate stable cell lines, individual cells can be isolated from the pools and cultured (a process referred to as cloning), a laborious time consuming process. However, in some instances, the pools them selves may be stable (i.e., production of the heterologous recombinant protein remains stable). The ability to select and culture such stable pools of cells is desirable as it allows rapid production of relatively large amounts of recombinant protein from *Acanthamoeba* cells.

Useful selectable markers for gene amplification include DHFR-MTX resistance, P-glycoprotein and multiple drug resistance (MDR)-various lipophilic cytoxic agents (i.e., adriamycin, colchicine, vincristine), and adenosine deaminase (ADA)-Xyl-A or adenosine and 2'-deoxycoformycin. Specific examples of genes that encode selectable markers are those that encode antimetabolite resistance such as the DHFR protein, which confers resistance to methotrexate (Wigler et al., 1980, Proc. Natl. Acad. Sci. USA 77:3567; O'Hare et al., 1981, Proc. Natl. Acad. Sci. USA 78:1527); the GPT protein, which confers resistance to mycophenolic acid (Mulligan & Berg, 1981, Proc. Natl. Acad. Sci. USA 78:2072), the neomycin resistance marker (the most preferred marker for use in the present invention), which confers resistance to the aminoglycoside G-418 (Colberre-Garapin et al., 1981, J. Mol. Biol. 150:1); the Hygro protein, which confers resistance to hygromycin (Santerre et al., 1984, Gene 30:147); and the Zeocin.TM. resistance marker (available commercially from Invitrogen). In addition, the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- and aprt-cells, respectively.

Uses of the Invention

As used herein, the term "heterologous protein" refers to a protein or polypeptide that is encoded by nucleic acid introduced into a host *Acanthamoeba* cell. The protein of interest may be expressed from a naturally occurring gene, a mutated gene or a synthetic gene. The term "homologous protein" refers to a protein or polypeptide that naturally occurs in the host *Acanthamoeba* cell. The present invention encompasses homologous proteins that are introduced into the host *Acanthamoeba* cell via recombinant means.

The inventive vectors and methods will find use for the expression of a wide variety of recombinant polypeptides. Examples of such polypeptides include cytokines and growth factors, such as Interleukins 1 through 18, the interferons, RANTES, lymphotoxin-b, Fas ligand, flt-3 ligand, ligand for receptor activator of NF-kappa B (RANKL), TNF-related apoptosis-inducing ligand (TRAIL), CD40 ligand, Ox40.ligand, 4–1BB ligand (and other members of the TNF family), thymic stroma-derived lymphopoietin, granulocyte colony stimulating factor, granulocyte-macrophage colony stimulating factor, mast cell-growth factor, stem cell growth factor, epidermal growth factor, growth hormone, tumor necrosis factor, leukemia inhibitory factor, oncostatin-M, and hematopoietic factors such as erythropoietin and thrombopoietin.

Also included are neurotrophic factors such as brain-derived neurotrophic factor, ciliary neurotrophic factor, glial cell-line derived neurotrophic factor and various ligands for cell surface molecules Elk and Hek (such as the ligands for eph-related kinases, or LERKS). Descriptions of proteins that can be expressed according to the inventive methods may be found in, for example, Human Cytokines: Handbook for Basic and Clinical Research, Vol. II (Aggarwal and Gutterman, eds. Blackwell Sciences, Cambridge Mass., 1998); Growth Factors:A Practical Approach (McKay and Leigh, eds., Oxford University Press Inc., New York, 1993) and The Cytokine Handbook (A W Thompson, ed.; Academic Press, San Diego Calif.; 1991).

Receptors for any of the aforementioned proteins may also be expressed using the inventive vectors and methods, including both forms of tumor necrosis factor receptor (referred to as p55 and p75), Interleukin-1 receptors (type 1 and 2), Interleukin-4 receptor, Interleukin-15 receptor, Interleukin-17 receptor, Interleukin-18 receptor, granulocyte-macrophage colony stimulating factor receptor, granulocyte colony stimulating factor receptor, receptors for oncostatin-M and leukemia inhibitory factor, receptor activator of NF-kappa B (RANK), receptors for TRAIL, and receptors that comprise death domains, such as Fas or Apoptosis-Inducing Receptor (AIR).

Other proteins that can be expressed using the inventive vectors and methods include cluster of differentiation antigens (referred to as CD proteins), for example, those disclosed in Leukocyte Typing VI (Proceedings of the VIth International Workshop and Conference; Kishimoto, Kikutani et al., eds.; Kobe, Japan, 1996), or CD molecules disclosed in subsequent workshops. Examples of such molecules include CD27, CD30, CD39, CD40; and ligands thereto (CD27 ligand, CD30 ligand and CD40 ligand). Several of these are members of the TNF receptor family, which also includes 41BB and Ox40; the ligands are often members of the TNF family (as are 4–1BB ligand and Ox40 ligand); accordingly, members of the TNF and TNFR families can also be expressed using the present invention.

Proteins that are enzymatically active-can also be expressed according to the instant invention. Examples include metalloproteinase-disintegrin family members, various kinases (including streptokinase and tissue plasminogen activator as well as Death Associated Kinase Containing Ankyrin Repeats, and IKR 1 and 2), TNF-alpha Converting Enzyme, restriction enzymes, DNA-modifying enzymes and numerous other enzymes. Ligands for enzymatically active proteins can also be expressed by applying the instant invention.

The inventive vectors and methods are also useful for expression of other types of recombinant proteins, including immunoglobulin molecules or portions thereof, and chimeric antibodies (i.e., an antibody having a human constant region couples to a murine antigen binding region) or fragments thereof. Numerous techniques are known by which DNA encoding immunoglobulin molecules can be manipulated to yield DNAs capable of encoding recombinant proteins such as single chain antibodies, antibodies with enhanced affinity, or other antibody-based polypeptides (see, for example, Larrick et al., Biotechnology 7:934–938, 1989; Reichmann et al., Nature 332:323–327, 1988; Roberts et al., Nature 328:731–734, 1987; Verhoeyen et al., Science 239:1534–1536, 1988; Chaudhary et al., Nature 339:394–397, 1989).

Various fusion proteins can also be expressed using the inventive methods and vectors. Examples of such fusion proteins include proteins expressed as fusion with a portion of an immunoglobulin molecule, proteins expressed as fusion proteins with a zipper moiety, and novel polyfunctional proteins such as a fusion proteins of a cytokine and a growth factor (i.e., GM-CSF and IL-3, MGF and IL-3). WO 93/08207 and WO 96/40918 describe the preparation of various soluble oligomeric forms of a molecule referred to as CD40L, including an immunoglobulin fusion protein and a zipper fusion protein, respectively; the techniques discussed therein are readily applicable to other proteins.

As additional examples, DNAs based on one or more expressed sequence tag (EST) from a library of ESTs can be prepared, inserted into the inventive vector and expressed to obtain recombinant polypeptide. Moreover, DNAs isolated by use of ESTs (i.e., by PCR or the application of other cloning techniques) can also be expressed by applying the instant invention. Information on the aforementioned polypeptides, as well as many others, can be obtained from a variety of public sources, including electronic databases such as GenBank. A particularly useful site is the website of the National Center for Biotechnology Information/National Library of Medicine/National Institutes of Health. Those of ordinary skill in the art are able to obtain information needed to express a desired polypeptide and apply the techniques described herein by routine experimentation.

The present invention provides a for a stable expression system for the production of a vaccine which may be used therapeutically or prophylactically. Accordingly, the invention extends to the production of vaccines containing heterologous nucleic acid which, preferably, encodes an antigenic or immunogenic polypeptide.

However, for purposes of this application, the definition of a protein of interest excludes genes encoding proteins that are typically used as selectable markers in cell culture such as auxotrophic, antimetabolite and/or antibiotic markers. Nevertheless, the invention does include the use of a selectable marker as an aid in selecting cells and/or amplifying clones that are genetically engineered to express a gene of interest. Preferably, the selectable marker gene is positioned adjacent to the gene of interest such that selection and/or amplification of the marker gene will select and/or amplify the adjacent gene.

The invention also provides a kit for expressing a desired protein of interest comprising a stable expression system for production of a protein comprising: a) a host organism selected from the group consisting of the species of *Acanthamoeba*; b) a DNA vector which comprises a selection marker gene which codes -for a protein which, after transformation of the host organism, allows selection of positive transformants and is selected from the group consisting of antibiotic resistance genes or of genes which encode proteins which are capable of a color-forming reaction, where expression of the selection marker gene is controlled by at least one genetic regulatory element which is homologous in the host organism; and c) a DNA vector which comprises a heterologous gene for the expression of a heterologous protein, where the expression of the protein is controlled by at least one genetic regulatory element which is homologous to the host organism.

Isolating and Purifying Expressed Proteins

The isolation and purification of proteins expressed for the stable *Acanthamoeba* expression systems of the present invention are methods well know in the art. For example, proteins of interest can be tagged with the flu-virus HA epitope TAG as well as a Hexa-Histidine TAG. This permits their purification either by immunoprecipitation using a commercially available monoclonal antibody against the HA tag, or alternatively by the now routine Nickel affinity chromatography in the same fashion as proteins made in *E. coli*. Other TAGs could also be used.

Storage of Stable *Acanthamoeba* Expression Systems in Cyst Formation

One of the advantages of the present invention relates to a form of a stable *Acanthamoeba* expression system which allows the system to be stored in a non-aqueous, cyst form at temperature ranges between 50 and 120° F. As such, this sytem is highly transportable and offers the convenience of developing stable protein expression systems without specific and elaborate conditions for transportation or storage.

The relevant disclosures of all references cited herein are specifically incorporated by reference. The following examples are intended to illustrate particular embodiments, and not limit the scope, of the invention. Those of ordinary skill in the art will readily recognize that additional embodiments are encompassed by the invention.

EXAMPLES

The following materials and methods were used in the Examples:

Experimental Procedures

Growth and Transfection of *Acanthamoeba*

*Acanthamoeba* were grown routinely in shake culture using standard medium (38), at 200 rpm at 30° C. Prior to transfection, $5\times10^5$ cells were centrifuged at 1000 g for 5 minutes and the media removed. Cells were resuspended in 500 μl of encystment medium (39) and placed in a 6 well culture dish (Falcon). DNA was prepared for transfection as follows. 4 μg of supercoiled plasmid DNA, in a volume of 3 to 6' μl, was diluted in 100 μl of encystment medium. 20 μl of Superfect reagent (Qiagen) was added and the solution mixed by gently pipetting up and down 5 times. After a ten minute incubation at room temperature, 600 μl of encystment medium was added and the mixture was added to the cells in a six well culture dish to give a final volume of 1200 μl. Incubation was continued for three hours at 28° C., after which the transfection solution was removed by pipetting, and any dislodged cells were recovered by centrifugation. Transfected cells were allowed to recover for twenty four hours at 28° C. in 4 ml of growth medium, and then transferred into 25 ml of growth media containing 50 μg neomycin G418/ml in a 50 ml shake flask and cultured as described above. After several days, cell growth becomes apparent, and cells can be passaged in the same manner as untransfected cells.

The CSP21 gene promoter was induced by harvesting transfected cells, washing, and resuspending them at a density of $5\times10^5$ cells/ml in encystment medium containing neomycin. Cells were viewed microscopically at the time intervals described in the appropriate figure legends, or harvested for lysate preparation and Western analysis.

Construction of Plasmids for Transfection p-110Neo (see FIG. 1) was constructed by inserting the *Acanthamoeba* TBP promoter (−110 to +68) with an EcoRV site at both ends generated from pAgTFIID (40) into the StuI site of pCI-EGFP (a gift of Drs. John Cherry and Greg Gilmartin of this department). The CMV-I promoter of p-110Neo was replaced with an Acc651-NcoI fragment from the TBP promoter containing sequences from either −110 or −50 to +68 to generate p-110EGFP (Neo) and p-50EGFP (Neo), respectively (see FIG. 2). pCSP21EGFP(Neo) was constructed by similar procedures but inserting an Acc651-NcoI fragment of the CSP21 promoter (−400-+59) from pCSP-FL (11) in place of the CMV promoter (see FIG. 4). A BsrGI-XbaI fragment containing full length TBP encoding sequences (41) and a 5'HA-6His tag (SEQ ID NO: 3) from pET3AFHTBP was cloned into digested p-110EGFP (Neo) to construct p-110EGFPFHTBP(Neo) (see FIG. 3). The protein tag encoded at the N-terminus of the pET3AFHTBP cDNA in is: MGYPYDVPDYAVHHHHHH (SEQ ID NO: 4). The structure of each construct was confirmed by sequencing. All the inserts described above were generated by PCR essentially as described previously (5) with the following oligonucleotide primers:

```
TBP - 110EcoRV:   CAGATATCAAACGACGCCTTGCAACAAG (forward);      (SEQ ID NO: 5)

TBP + 68EcoRV:    CAGATATCTTGTTGTATGTGTGAATCGAC (reverse);     (SEQ ID NO: 6)

TBP - 110Acc651:  GAGGTACCAAACGACGCCTTGCAACAAG (forward);      (SEQ ID NO: 7)

TBP - 50Acc651:   GAGGTACCGAAACGTTGGCATCACCGGG (forward);      (SEQ ID NO: 8)

TBP + 68Nco1:     CGACCATGGCTTGTTGTATGTGTGAATCGAC (reverse);   (SEQ ID NO: 9)

BsrGI - FH-TBP:   GCTGTACAAGTACCCCTACGACGTGCCCGACTAC (forward); (SEQ ID NO: 10)

XbaI - TBPc-CT:   GCTCTAGAGTCGCGGCCGCTTTAGGTCTTCTTGTACTC (reverse); (SEQ ID NO: 11)

CSP21 - 400Acc651: GATCCGGTACCCAACTCTACAAGACCACTTTCG (forward); (SEQ ID NO: 12)

CSP21ATGNcoI:     GGATCCCATGGCTTCAGATAGTTGGTAGTAGG (reverse).  (SEQ ID NO: 13)
```

Preparation of Lysates and Western Analysis of Transfected Cells

Transfected cell lines were harvested by centrifugation at 1000 g for five minutes and 100 µl packed cell pellets were lysed by Dounce homogenization in lysis buffer containing protease inhibitors as described previously (42). Samples were centrifuged at 10,000 rpm to remove insoluble debris and normalized for protein concentration by a Coomassie Blue assay (BioRad). Cells that had formed cysts were disrupted by sonication at 4° C. for three minutes in one minute bursts. For analysis of nuclear proteins in some experiments, the insoluble nuclear pellet was extracted with lysis buffer containing 0.4M $(NH_4)_2SO_4$ in order to dissociate TBP from DNA, and proteins in the resulting nuclear fraction were precipitated with chloroform and methanol to remove salt prior to electrophoresis. SDS PAGE and Western analysis was done using standard procedures (43).

Microscopy

Live cells were viewed using a Zeiss Axiovert 40 inverted microscope equipped with a 40× fluorescence objective or a 40× Plas DIC objective. Cells were viewed in either a six well tissue culture tray or on multi-test slides and photographed using a Sony DXC-S500 color digital camera.

Preparation of DNA

Acanthamoeba genomic DNA from control or transfected cells was prepared as described previously (44), and stored in ethanol at −20° C. PCR and Southern analysis were done using standard procedures (45, 46) using the probes and primers described in the appropriate figure legend. Plasmids were prepared using Qiagen kits.

Example 1

Sensitivity of Acanthamoeba to Neomycin G418.

As a preliminary experiment, the sensitivity of untransfected Acanthamoeba to neomycin G418 was examined by culturing cells in the presence of varying concentrations of neomycin G418. Concentrations of neomycin G418 at or above 10 µg/ml were found to completely inhibit cell growth (not shown). Growth is inhibited to a lesser extent by 5 µg neomycin/ml. After extended periods in the presence of neomycin G418, cells die as evidenced by lysis and loss of visible cells (not shown). In order to ensure complete suppression of growth during transfection experiments, selection for neomycin G418 resistance was done at 50 µg neomycin/ml unless otherwise noted.

Example 2

Figure 1B:
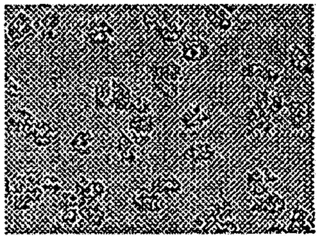
Figure 1C:
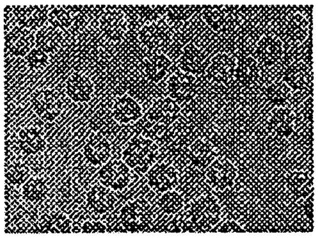
Figure 1D:
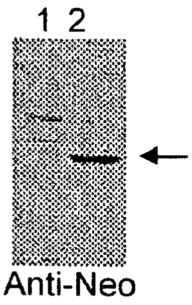
Figure 2A:
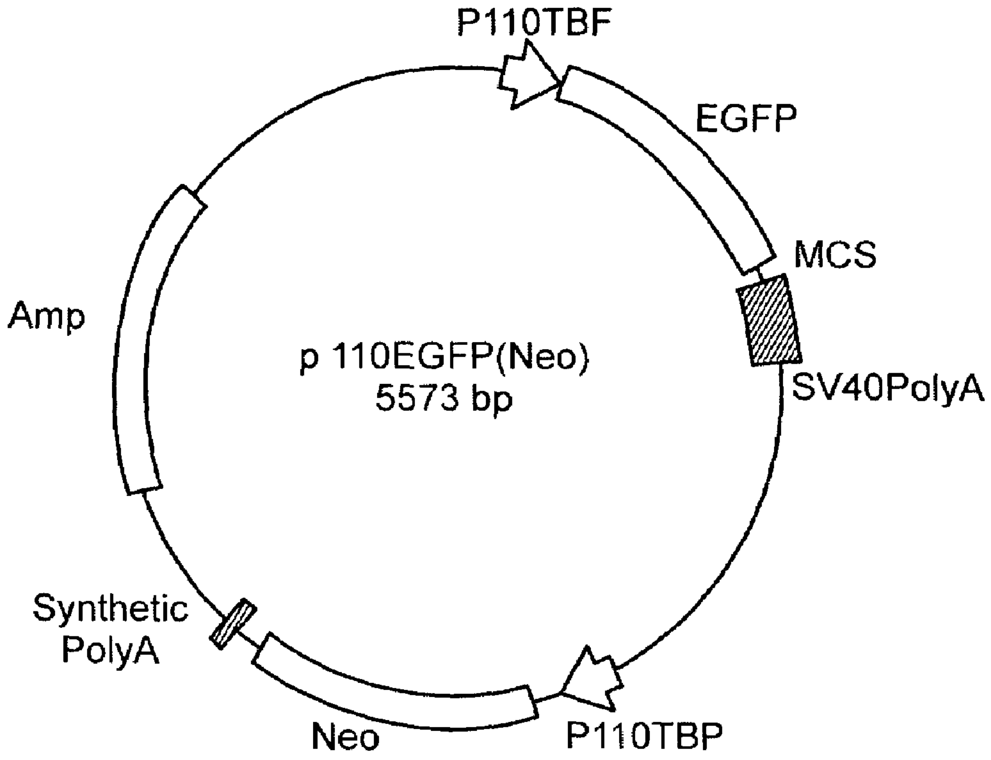
FIG. 2 represents a) diagram of p-110EGFP(Neo) showing the position of the TBP promoter driving EGFP expression; b) DIC photomicrograph of cells transfected with p-110EGFP(Neo); c) Same field as B taken using a fluorescence objective; e) Diagram of plasmid p-50EGFP(Neo); f) DIC photomicrograph of cells transfected with p-50EGFP (Neo); g) Same field as E taken using a fluorescence objective; Panels d and h; Western analysis of EGFP expression from cells transfected with p-110EGFP(Neo) or p-50EGFP(Neo); Lanes 1, control untransfected cell lysates; lanes 2, lysates from cells transfected with p-110EGFP (Neo); lanes 3, lysates from cells transfected with p-50EGFP (Neo). Blots were probed with the antibodies indicated.
Figure 2E:
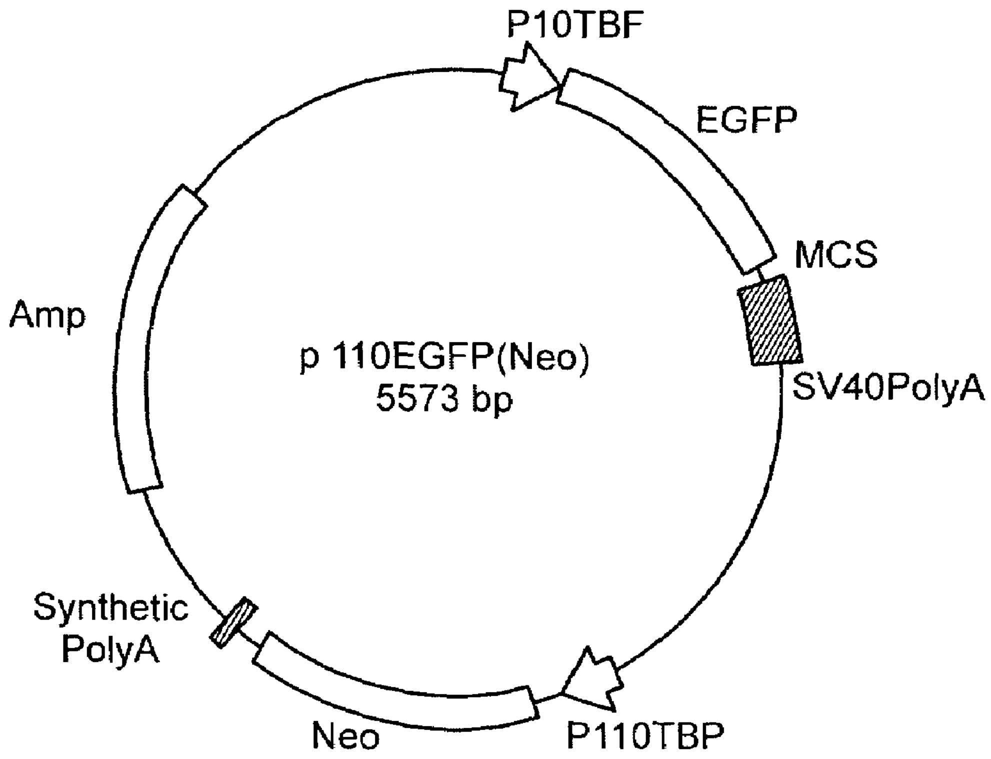
Figure 2B:
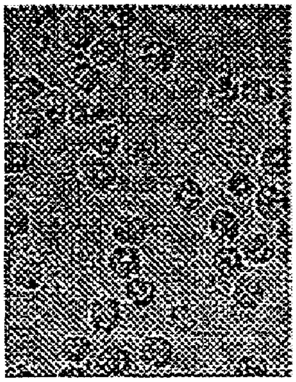
Figure 2C:
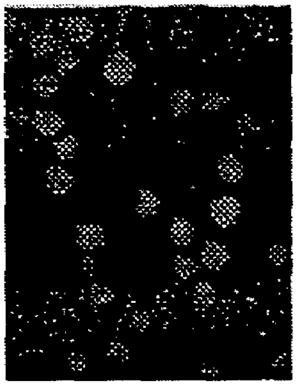
Figure 2D:
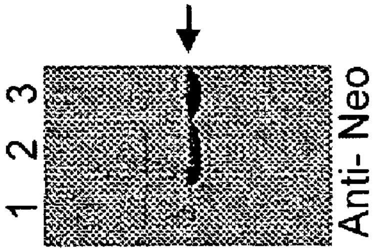
Figure 2F:
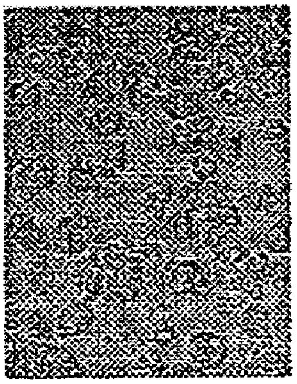
Figure 2G:
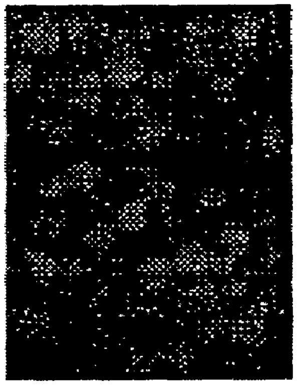
Figure 2H:
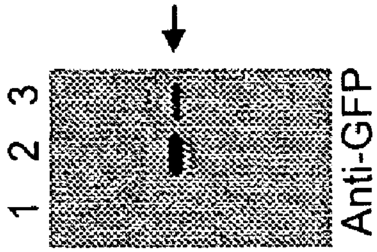
Figure 3A:
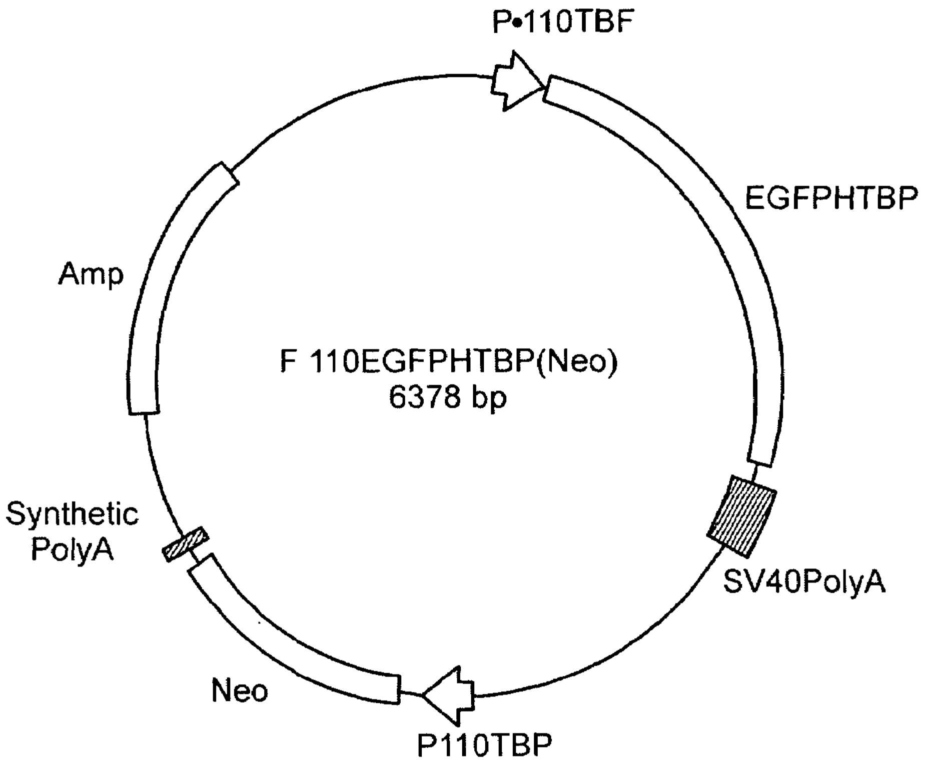
FIG. 3 represents a) diagram of plasmid p-110EGFPFHTBP(Neo) showing the placement of the EGFP-Flag/His-TBP fusion; b) DIC photomicrograph of cells transfected with p-110EGFPFHTBP(Neo); c) Fluorescence micrograph of cells transfected with p-110EGFPFHTBP(Neo) showing nuclear localization of the EGFP/TBP fusion. The images in B and C are from different fields of cells within the same sample; Panels d, e and f show Western blots of lysates from control cells (lanes 1) or cells transfected with p-110EGFPFHTBP(Neo) (lanes 2) and probed with the indicated antibodies; the lower arrow in panel F indicates the band corresponding to endogenous TBP.
Figure 3B:
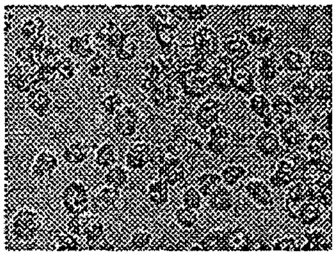
Figure 3C:
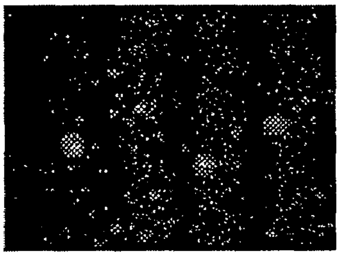
Figure 3D:
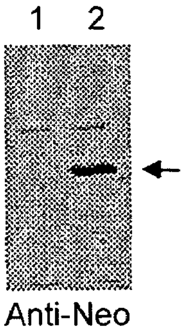
Figure 3E:
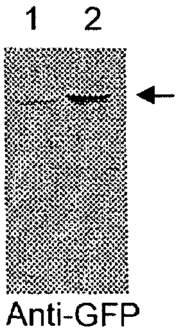
Figure 3F:
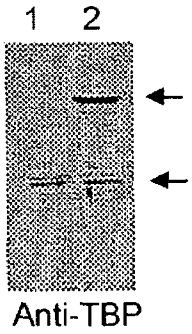

Stable Transfection of Acanthamoeba and Expression of Neomycin Phosphotransferase The Acanthamoeba TBP gene promoter from −110 to the ATG initiation codon (+68) was inserted within the SV40 promoter upstream of the neomycin phosphotransferase gene in plasmid pCI-EGFP (FIG. 1) to generate the plasmid p-110Neo. The Acanthamoeba TBP gene promoter was used because it has been thoroughly characterized in vitro (10, 13, 40, 47, 48) and because the viral promoters present in pCI-EGFP are not functional in Acanthamoeba (not shown). Acanthamoeba were transfected with p-110Neo and grown in medium containing 50 µg neomycin G418/ml. After several days, cell growth became apparent as determined microscopically. Cells were transferred to fresh neomycin G418-containing medium and grown and passaged several times. Transfected cells are quite normal in appearance, but are rather rounded when compared to control cells grown in the absence of neomycin G418 (FIGS. 1B and C). Transfected cells have an increased cell division cycle of approximately 12 h vs 6 h for untransfected amoebae.

In order to demonstrate that growth is due to expression of neomycin phosphotransferase, rather than acquisition of resistance by some other means (49), equivalent numbers of control or transfected cells were harvested and expression of neomycin phosphotransferase was measured by Western blotting. As shown in FIG. 1, lysates from transfected cells produce a strong signal corresponding to neomycin phosphotransferase, whereas lysates from control cells produce no signal above background. We infer that transfection with p-110Neo results in cells capable of growth in the presence of neomycin G418 due to expression of neomycin phosphotransferase. All cell lines generated using plasmids derived from p-110Neo also produced neomycin phosphotransferase, as expected (see below).

Example 3

Expression of Neomycin Phosphotransferase and EGFP

While the experiments described above provide a proof of concept for stable transfection, they formally left open the possibility that only some cells are transfected, and resistance in the population as a whole was a consequence of inactivation of neomycin G418 by a sub-population. In addition, for stable transfection to be useful, expression of a second reporter gene is necessary in order to examine promoter structures or express proteins other than neomycin phosphotransferase. We therefore added a cassette containing the EGFP coding region (50, 51) downstream from a second copy of the *Acanthamoeba* TBP gene promoter to produce the EGFP and neomycin phosphotransferase expression vector p-110EGFP(Neo) (FIG. 2). Cells transfected with this vector are similar in appearance to those expressing neomycin phosphotransferase alone, but have a more rapid growth rate (8 h) and express both EGFP and neomycin phosphotransferase as determined by fluorescence microscopy and Western analysis (FIG. 2). Microscopy clearly demonstrates that all cells within the population are transfected, and most cells show moderate fluorescence. Cells transfected with p-110EGFP(Neo) are also rather rounded in appearance, and show a marked tendency to become completely rounded in ageing cultures (not shown), suggesting that expression of either neomycin phosphotransferase or EGFP produces some stress to cells. A small number of cells are extremely bright and we have observed this pattern using other constructs (not shown). We suggest that the far more common, moderately fluorescent cells are most relevant to the strength of the TBP gene promoter, which is not expected to be particularly robust, based on the low abundance of TBP mRNA represented in a cDNA library (41). These results clearly demonstrate the ability to express two proteins driven by different promoters on the same plasmid.

Cells transfected with p-50EGFP(Neo) are similar in overall behavior as those transfected with p-110EGFP(Neo), except that they express EGFP at a reduced level as evidenced by lower fluorescence when viewed microscopically or by Western analysis (FIG. 2). The −50 deletion to the TBP promoter in this construct is lacking a stimulatory element, the TPE, found to be important for in vitro transcription (48), therefore this result is entirely consistent with previous in vitro experiments.

Example 4

Expression of a TBP-EGFP Fusion Protein in *Acanthamoeba*

In order to determine whether a physiologically relevant protein could be expressed in a regulated fashion, and whether the system is responsive to normal cellular localization and other cues, we constructed a fusion between EGFP and the *Acanthamoeba* transcription factor TBP (p-110EGFPFHTBP(Neo), (FIG. 3). Cells transfected with p-110EGFPFHTBP(Neo) were grown and processed as for neo/EGFP only cells (above), and expression of the EGFP-TBP fusion was examined by microscopy and Western analysis. Microscopic analysis shows that most cells express the EGFP fusion, but that it is concentrated within the nucleus, as expected for TBP (FIG. 3C). Expression of the EGFP-TBP fusion protein is also readily demonstrated by Western analysis of cell lysates using antibodies directed against TBP or EGFP which visualize a protein with an apparent molecular weight of ~60,000, the expected size for the fusion protein (FIGS. 3E and F). The level of expression of the TBP-GFP fusion is apparently reduced when compared to that of EGFP alone. Similarly, the level of endogenous TBP is also reduced in cells transfected with the EGFP/TBP fusion. A similar result was obtained with nuclear extracts (not shown).

Example 5

Developmentally Regulated Expression from the CSP21 Gene Promoter

Figure 4A:
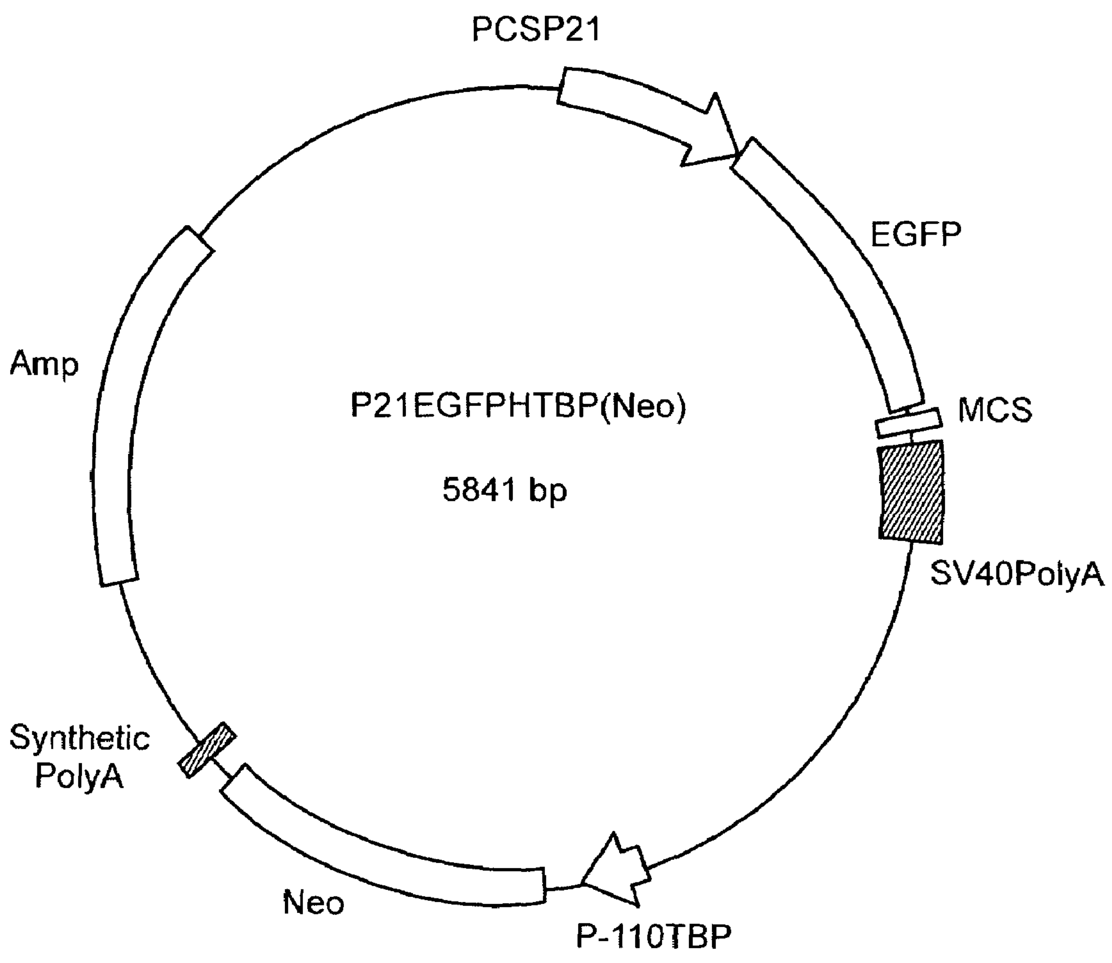
FIG. 4 represents a) diagram of plasmid p21EGFP(Neo) showing the placement of the CSP21 gene promoter (PCSP21). Panels b and c show Western blots of lysates from cells transfected with p21EGFP(Neo) and induced to differentiate by starvation for 0 hours or 24 hours as indicated; the blots were probed with anti-neomycin phosphotransferase or anti GFP as indicated.

The promoter for the *Acanthamoeba* gene encoding cyst specific protein 21 is tightly repressed during cell growth and is induced within the first twelve hours of starvation-induced differentiation (11, 52). In order to determine whether stably transfected genes can be correctly repressed and induced, we replaced the TBP gene promoter in p-110EGFP(Neo) with the CSP21 gene promoter (FIG. 4) and used the resulting construct to stably transfect *Acanthamoeba*. If the transfected promoter is properly regulated, it is expected to be completely silent during growth, and EGFP should only be produced when cells are induced to differentiate. As shown in FIGS. 4 and 5, EGFP is undetectable in growing transfected cells but is strongly induced after 24 hours of differentiation as determined by Western analysis and microscopy. It can be inferred that the transfected CSP21 gene promoter is regulated in the same manner as its endogenous counterpart.

Figure 4B:
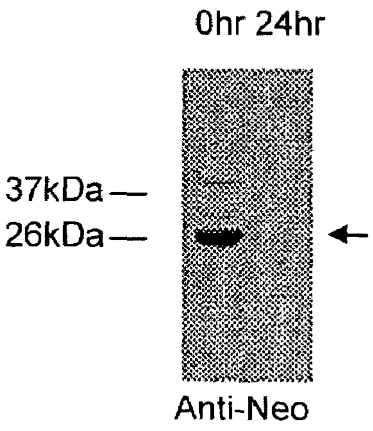
Figure 4C:
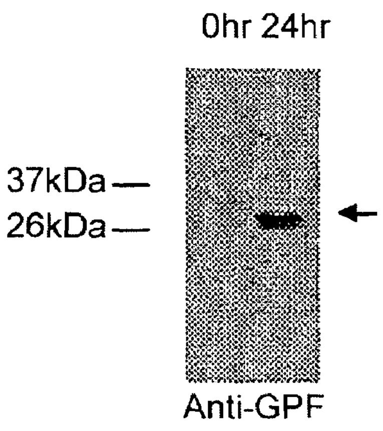
Figure 5:
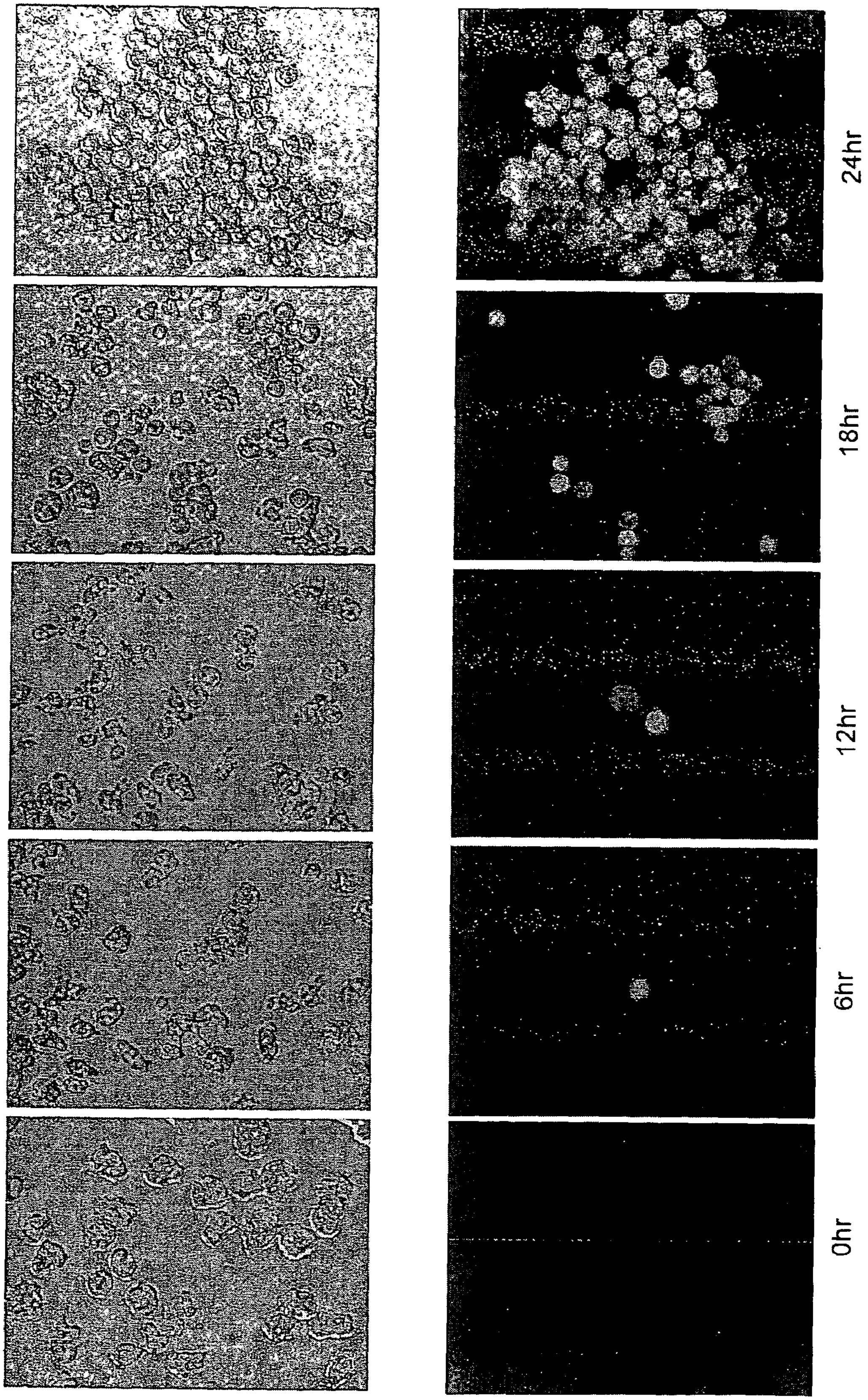
FIG. 5 represents a time course of CSP21 promoter induction; cells transfected with plasmid p21EGFP(Neo) were induced to differentiate by starvation for the times indicated at the bottom of the figure; the upper series shows DIC images; the lower series shows fluorescence images of matched fields.

Although EGFP expression driven by the CSP21 promoter is strongly induced, we were surprised to notice that neomycin phosphotransferase expression is completely repressed during cyst formation, and apparently is degraded since it is undetectable by Western analysis (FIG. 4B). This result explains our inability to grow transfected cysts in the presence of neomycin (see below), since mature cysts lack neomycin phosphotransferase.

Example 6

Stability of Transfected Phenotypes

Transfection of cells with plasmids can result in extrachromosomal maintenance and replication of the plasmid or integration within the host genome. In the former case, plasmids may be lost in the absence of selective pressure, whereas integrated DNA is expected to be maintained indefinitely, providing that it does not exert a negative selective pressure. The stability of the transfected phenotypes during growth was examined by passaging cells in the absence of neomycin G418 and stability during differentiation was examined by inducing cyst-formation, then regrowing the cells. Cells stably transfected with p-110EGFP (Neo) vector were grown in the absence of neomycin and monitored by microscopy. Expression of EGFP is stable in the absence of selection for at least five weeks, which corresponds to over 100 cell divisions. In addition, differentiated cells that were regrown from cysts that had been stored at room temperature for several weeks expressed EGFP, although cells temporarily lose the ability to express neomycin phosphotransferase or EGFP when they encyst, requiring that neomycin be omitted from the growth medium when cells are grown from cysts.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

REFERENCES

1. Byers, T. J. (1979) *International Review of Cytology* 61,283–338.
2. Marciano-Cabral, F., Puffenbarger, R. & Cabral, G. A. (2000) *J. Eukaryot. Microbiol.* 47, 29–36.
3. Winiecka-Krusnell, J. & Linder, E. (2001) *Res. Microbiol.* 152, 613–619.
4. Matthews, J. L., Zwick, M. G. & Paule, M. R. (1995) *Molec. Cell Biol.* 15, 3327–3335.
5. Peng, Z. & Bateman, E. (2004) *Molec. Microbiol.* 52, 1123–1132.
6. Radebaugh, C. A., Matthews, J. L., Geiss, G. K., Liu, F., Wong, J. -M., Bateman, E., Camier, S., Sentenac, A. & Paule, M. R. (1994) *Molec. Cell. Biol.* 14, 597–605.
7. Paule, M. R. & White, R. J. (2000) *Nucleic Acids Res.* 28, 1283–1298.
8. Bateman, E. & Paule, M. R. (1986) *Cell* 47, 445–450.
9. Kahl, B. F., Li, H. & Paule, M. R. (2000) *Journal of Molecular Biology* 299, 75–89.
10. Chen, L., Peng, Z. & Bateman, E. (2004) *Nucleic Acids Res.* 32, 1–10.
11. Chen, L., Orfeo, T., Gilmartin, G. & Bateman, E. (2004) *Biochim. Biophys. Acta* 1691, 23–31.
12. Huang, W. & Bateman, E. (1995) *J. Biol. Chem.* 270, 28839–28847.
13. Bateman, E. (1998) *Prog. Nucleic Acids Res. Molec. Biol.* 60, 133–168.
14. Kaiser, D. A., Vinson, V. K., Murphy, D. B. & Pollard, T. D. (1999) *J. Cell Sci.* 112, 3779–3790.
15. Ostap, E. M., Maupin, P., Doberstein, S. K., Baines, I. C., Korn, E. D. & Pollard, T. D. (2003) *Cell Motil. Cytoskeleton* 54, 29–40.
16. Pollard, T. D. & Beltzner, C. C. (2002) *Curr. Opin. Struct. Biol.* 12, 768–774.
17. Pollard, T. D. & Rimm, D. L. (1991) *Cell Motility Cytoskel.* 20, 169–177.
18. Shu, S., Liu, X. & Korn, E. D. (2003) *Proc. Natl. Acad. Sci. U.S.A* 100, 6499–6504.
19. Liu, X., Brzeska, H. & Korn, E. D. (2000) *J. Biol. Chem.* 275, 24886–24892.
20. Brzeska, H., Young, R., Tan, C., Szczepanowska, J. & Korn, E. D. (2001) *J. Biol. Chem.* 276, 47468–47473.
21. Remmert, K., Olszewski, T. E., Bowers, M. B., Dimitrova, M., Ginsburg, A. & Hammer, J. A., III (2004) *J. Biol. Chem.* 279, 3068–3077.
22. Redowicz, M. J., Hammer, J. A., III, Bowers, B., Zolkiewski, M., Ginsburg, A., Korn, E. D. & Rau, D. C. (1999) *Biochemistry* 38, 7243–7252.
23. Wang, Z. Y., Wang, F., Sellers, J. R., Korn, E. D. & Hammer, J. A., III (1998) *Proc. Natl. Acad. Sci. U.S.A* 95, 15200–15205.
24. Ostap, E. M., Lin, T., Rosenfeld, S. S. & Tang, N. (2002) *Biochemistry* 41, 12450–12456.
25. Niederkorn, J. Y., Alizadeh, H., Leher, H. & McCulley, J. P. (1999) *Microbes Infect.* 1, 437–443.
26. Cao, Z., Jefferson, D. M. & Panjwani, N. (1998) *J. Biol. Chem.* 273, 15838–15845.
27. Yang, Z., Cao, Z. & Panjwani, N. (1997) *Infect. Immun.* 65, 439–445.
28. Marciano-Cabral, F. & Toney, D. M. (1998) *J. Eukaryot. Microbiol.* 45, 452–458.
29. Marciano-Cabral, F. & Cabral, G. (2003) *Clin. Microbiol. Rev.* 16, 273–307.
30. Byers, T. J. (1986) *International Review of Cytology* 99, 311–341.
31. Byers, T. J., Hugo, E. R. & Stewart, V. J. (1990) *J. Protozool.* 37, 17S–25S.
32. Gast, R. J., Ledee, D. R., Fuerst, P. A. & Byers, T. J. (1996) *J. Eukaryot. Microbiol* 43, 498–504.
33. Booton, G. C., Rogerson, A., Bonilla, T. D., Seal, D. V, Kelly, D. J., Beattie, T. K., Tomlinson, A., Lares-Villa, F., Fuerst, P. A. & Byers, T. J. (2004) *J. Eukaryot. Microbiol* 51, 192–200.
34. Gast, R. J. & Byers, T. J. (1995) *Mol. Biochem. Parasitol.* 71, 255–260.
35. Batzri, S. & Korn, E. D. (1975) *J. Cell Biol.* 66, 621–634.
36. Yin, J. & Henney, H. R. (1996) *Can. J. Microbiol.* 43, 239–244.
37. Hu, A. & Henney, H. R. (1997) *Biochim. Biophys. Acta.* 1351, 126–136.
38. Kong, H.-Y. & Pollard, T. D. (2002) *J. Cell Sci.* 115, 4993–5002.
39. Neff, R. J., Ray, S. A., Benton, W. F. & Wilborn, M. (1964) *Methods in Cell Physiology* 1, 55–83.
40. Wong, J. M., Liu, F. & Bateman, E. (1992) *Nucleic Acids Res.* 20, 4817–4824.
41. Wong, J. M., Liu, F. & Bateman, E. (1992) *Gene* 117,91–97.
42. Liu, F. & Bateman, E. (1992) *Gene* 120, 143–149.
43. Harlow, E. & Lane, D. (1988) *Antibodies. A laboratory manual*. (Cold Spring Harbor Laboratory Press, Cold Spring Harbor).
44. Hammer, J. A., Korn, E. D. & Paterson, B. M. (1986) *J. Biol. Chem.* 261, 1949–1956.
45. Sambrook, J., Fritsch, E. F. & Maniatis, T. (1989) *Molecular Cloning. A Laboratory Manual*. (Cold Spring Harbor Laboratory Press, Cold Spring Harbor).
46. Ausubel, F. M., Brent, R., Kingston, R. E., Moore, D. D., Seidman, J. G., Smith, J. A. & Struhl, K. (1989) *Current protocols in molecular biology*. (Greene Publishing Associates and Wiley Interscience, New York).
47. Huang, W. & Bateman, E. (1997) *J. Biol. Chem.* 272, 3852–3859.
48. Liu, F. & Bateman, E. (1993) *Nucleic Acids Res.* 21, 4321–4329.
49. Seilhamer, J. J. & Byers, T. J. (1982) *J. Protozool.* 29, 394–397.
50. Heim, R., Prasher, D. C. & Tsien, R. Y. (1994) *Proc. Natl. Acad. Sci. USA* 91, 12501–12504.
51. Zhang, G., Gurtu, V. & Kain, S. R. (1996) *Biochem. Biophys. Res. Commun.* 227, 707–711.
52. Hirukawa, Y., Nakato, H., Izumi, S., Tsuruhara, T. & Tomino, S. (1998) *Biochim. Biophys. Acta* 1398, 47–56.
53. Liu, F. & Bateman, E. (1994) *J. Biol. Chem.* 269, 18541–18548.
54. Ngo, H., Tschudi, C., Gull, K. & Ullu, E. (1998) *Proc. Natl. Acad. Sci. U.S.A* 95, 14687–14692.
55. Nishikura, K. (2001) *Cell* 107, 415–418.
56. Orfeo, T. & Bateman, E. (1998) *Biochim. Biophys. Acta* 1443, 297–304.

I claim:

1. A stable expression system for production of a protein comprising:

a) a host organism selected from the group consisting of the species of *Acanthamoeba;* b) a DNA vector which comprises a selection marker gene which codes for a protein which, after transformation of the host organism, allows selection of positive transformants and is selected from the group consisting of antibiotic resistance genes or of genes which encode proteins which are capable of a color-forming reaction, where expression of the selection marker gene is controlled by at least one genetic regulatory element which is homologous to the host organism; and c) a DNA vector which comprises a heterologous gene for the expression ora heterologous protein, where the expression of the protein is controlled by at least one genetic regulatory element which is homologous to the host organism.

2. A stable expression system of claim 1, wherein the host organism is *Acanthamoeba castellanii.*

3. A stable expression system of claim 1, wherein the selectable marker gene is the gene encoding neomycin phosphotransferase.

4. A stable expression system of claim 1, wherein the genetic regulatory element active in the host organism is selected from the group consisting of the promoter for the TBP gene and the promoter for the CSP21 gene.

5. A stable expression system of claim 1, wherein the protein to be expressed is a human polypeptide.

6. A process for production of a protein, which comprises:

a) obtaining an expression system of claim 1;

b) cultivating the expression system under appropriate culture media conditions; and c) isolating the protein from the culture media.

7. A kit for expressing a protein of interest comprising a stable expression system of claim 1.

8. A process for production of a protein, which comprises obtaining an expression system of claim 1, wherein following transformation of the vectors into the species of *Acanthamoeba*, the species is induced into cyst formation by exposure to differentiation conditions.

9. A stable expression system of claim 4, wherein the promoter for the TBP gene or the promoter for the CSP21 gene is a deletion mutant of said promoters.

10. A first DNA vector which comprises at least one selection marker gene which codes for a protein which, after stable transformation into a host organism selected from the group of species consisting of *Acanthamoeba*, allows selection of positive transformants, wherein the selection marker gene is selected from the group consisting of antibiotic resistance genes and genes which encode proteins which are capable of a color-forming reaction, and wherein the selection marker gene is controlled by at least one genetic regulatory element homologous to the host.

11. A DNA vector of claim 10 which further comprises a heterologous gene for the expression of a heterologous protein, where the expression of the protein is controlled by at least one homologous genetic regulatory element which is homologous to the host organism.

12. A kit for expressing a protein of interest comprising a DNA vector of claim 10.

13. A DNA vector of claims 10 or 11, wherein the genetic regulatory element active in the host organism is selected from the group consisting of the promoter for the TBP gene and the promoter for the CSP21 gene or a deletion mutant thereof.

14. A DNA vector of claim 13, wherein the TBP gene promoter comprises the base sequence present in SEQ ID NO:1.

15. A DNA vector of claim 13, wherein the CSP21 gene promoter comprises the base sequence present in SEQ ID NO:2.

16. A process for production of proteins, which comprises cultivating an *Acanthamoeba* species which has been prepared by a process as claimed in claim 6.

17. A kit of claim 7, wherein the kit includes a species of *Acanthamoeba* which has been induced into cyst formation by exposure to differentiation conditions.

18. A kit of claim 7, wherein the species of *Acanthamoeha* can be induced into cyst formation by exposure to differentiation conditions.

* * * * *